United States Patent
Wagner et al.

(10) Patent No.: US 10,092,370 B2
(45) Date of Patent: Oct. 9, 2018

(54) MEDICAL OR DENTAL HAND INSTRUMENT

(71) Applicant: W&H Dentalwerk Bürmoos GmbH, Bürmoos (AT)

(72) Inventors: Hannes Wagner, Salzburg (AT); Karlheinz Eder, Michaelbeuern (AT); Michael Rothenwaender, Lamprechtshausen (AT); Hermann Rehrl, Lamprechtshausen (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 641 days.

(21) Appl. No.: 14/626,858

(22) Filed: Feb. 19, 2015

(65) Prior Publication Data

US 2015/0230881 A1 Aug. 20, 2015

(30) Foreign Application Priority Data

Feb. 20, 2014 (EP) ..................................... 14155880

(51) Int. Cl.
*A61C 1/02* (2006.01)
*A61C 1/14* (2006.01)
*A61B 17/00* (2006.01)

(52) U.S. Cl.
CPC .............. *A61C 1/145* (2013.01); *A61B 17/00* (2013.01); *A61C 1/141* (2013.01); *A61B 2017/00477* (2013.01)

(58) Field of Classification Search
CPC . A61C 17/3472; A61C 17/3409; A61C 17/32; A61C 1/12; A61C 1/02
See application file for complete search history.

(56) References Cited

U.S. PATENT DOCUMENTS 2,100,319 A * 11/1937 Brown ............... A61B 17/1624
433/122
5,145,369 A * 9/1992 Lustig .................... A61C 17/00
433/118

(Continued)

FOREIGN PATENT DOCUMENTS

| EP | 1078606 | 2/2001 |
|---|---|---|
| EP | 1184002 | 3/2002 |
| WO | WO2013/076106 | 5/2013 |

*Primary Examiner* — Ralph Lewis
(74) *Attorney, Agent, or Firm* — Klarquist Sparkman, LLP

(57) ABSTRACT

A hand instrument, comprising: a tool-holding device for fastening a treatment tool on the hand instrument, a driveshaft for transmitting a driving movement to the tool-holding device and a stroke gear which is designed to induce the tool-holding device in a stroke movement. According to a first embodiment the hand instrument further has a rotary gear which is designed to induce the tool-holding device to a rotational movement, wherein a drive-side element of the rotary gear and a drive-side element of the stroke gear are arranged jointly on the driveshaft. According to a second embodiment the drive-side element of the stroke gear is designed such, that in a complete revolution of the drive-side element of the stroke gear the tool-holding device runs through more than a double stroke. According to another embodiment the drive-side element of the stroke gear is disposed concentrically around an axis of rotation of the driveshaft.

20 Claims, 2 Drawing Sheets

(56) References Cited

U.S. PATENT DOCUMENTS

| | | | |
|---|---|---|---|
| 5,974,615 A * | 11/1999 | Schwarz-Hartmann | ..................... A61C 17/3472 15/22.1 |
| 6,106,290 A * | 8/2000 | Weissman | ................ A61C 1/07 433/118 |
| 6,350,125 B1 * | 2/2002 | Matsutani | .............. A61C 1/185 433/118 |
| 6,629,842 B2 * | 10/2003 | Satake | .................. A61C 1/185 433/105 |
| 8,365,335 B2 * | 2/2013 | Fischer | ................. A61C 17/34 15/22.1 |
| 2013/0101958 A1 * | 4/2013 | Garcia | .................... A61C 1/06 433/122 |

\* cited by examiner

MEDICAL OR DENTAL HAND INSTRUMENT

CROSS REFERENCE TO RELATED APPLICATION

The present application claims priority from pending European Patent Application No. 14155880.9, filed Feb. 20, 2014, which is incorporated herein by reference.

BACKGROUND

Field

The present invention relates to a medical or dental hand instrument, in which the tool-holding device can be induced to a stroke movement.

Description of Prior Art

Patent Application WO 2013/076106 A2 discloses a medical, in particular dental, hand instrument, in which the tool-holding device can be induced to a simultaneous stroke and rotational movement. To transfer the rotational movement to the tool-holding device, a hollow shaft is provided, wherein on one end of the hollow shaft a gearwheel is disposed which engages another gearwheel on the tool-holding device. For generating the stroke movement an eccentric gear is provided having an eccentric pin and a recess that accommodates the eccentric pin on the tool-holding device. The eccentric pin is disposed on a second shaft, which is supported in the hollow shaft with the gearwheel. A stepdown gear is additionally provided for reducing the rotational speed of the hollow shaft and thus the tool-holding device as well, so that the rotational speed of the tool-holding device is reduced with respect to the stroke frequency.

SUMMARY

It is thus an object to create a medical or dental hand instrument having a tool-holding device that can be induced to a simultaneous stroke and rotational movement and having a gear that is simplified in comparison with the prior art for a simultaneous stroke and rotational drive of the tool-holding device. It is a further object to create a medical or dental hand instrument having an alternative stroke gear.

According to a first embodiment, the medical or dental hand instrument comprises: a tool-holding device for attachment, preferably releasable, of a treatment tool on the hand instrument wherein the tool-holding device can be induced to a simultaneous stroke and rotational movement, a rotary gear, which is designed to induce a rotational movement of the tool-holding device and a stroke gear, which is designed to induce a stroke movement of the tool-holding device. The rotary gear comprises at least one drive-side or drive element and one output-side or driven element that is provided on the tool-holding device, and the stroke gear comprises at least one drive-side or drive element and one output-side or driven element that is provided on the tool-holding device. The drive-side element of the rotary gear and the drive-side element of the stroke gear are disposed on a single, joint driveshaft. The design of the hand instrument and/or of the gear is thus greatly simplified while having the same function, i.e., simultaneous stroke and rotational driving of the tool-holding device. Additional advantages include simpler and less expensive production and assembly of the hand instrument and less space required in the interior of the hand instrument.

The tool-holding device and the two gears are disposed or designed in such a way that the tool-holding device can be induced to a simultaneous stroke and rotational movement. The phrase "simultaneous stroke and rotational movement" is understood to refer to a simultaneous rotating movement of the tool-holding device around an axis of rotation or a central axis of the tool-holding device and a stroke or reciprocating movement of the tool-holding device along its rotational axis or central axis. The stroke and rotary gears in particular are designed such, that the tool-holding device can be induced to a continuous and simultaneous stroke and rotational movement. A continuous and simultaneous stroke and rotational movement is understood to be a simultaneous rotating movement of the tool-holding device around an axis of rotation or a central axis of the tool-holding device as well as a stroke movement of the tool-holding device along its axis of rotation or central axis without (at least essentially) interrupting the stroke or rotational movement. The tool-holding device can thus be induced particularly preferably by the gears to execute a continuous and simultaneous stroke and rotational movement.

The stroke and rotary gears are disposed at the interface between the single, joint driveshaft and the tool-holding device or a driveshaft part comprising the tool-holding device. The stroke and rotary gears are preferably designed as separate gears, so that they generate and/or transmit the stroke movement and the rotational movement separately from one another, in particular through different components (hereinafter referred to as the first through fourth elements, for example). The stroke and rotary gears are disposed in particular in the connecting region between the head section and the handle part of the hand instrument.

The drive-side or drive element of the rotary gear comprises a first element and the drive-side or drive element of the stroke gear comprises a second, separate element and/or an element different from the first element. The first element or the drive-side element of the rotary gear comprises a gearwheel, for example. The second or drive-side element of the stroke gear comprises a pin, for example, in particular an elongated and/or cylindrical pin. The drive-side element of the rotary gear and the drive-side element of the stroke gear are preferably disposed or mounted on a joint base or on a joint (end) section of the single, joint driveshaft.

Preferably at least a portion of the drive-side element of the rotary gear and at least a portion of the drive-side element of the stroke gear are spaced a distance apart from one another. The drive-side element of the rotary gear and the drive-side element of the stroke gear are preferably spaced a distance apart from one another such that only the drive-side element of the rotary gear enters into a movement generating and/or transmitting connection with the output-side element of the rotary gear, and the drive-side element of the stroke gear enters into a movement generating and/or transferring connection with the output-side element of the stroke gear.

The drive-side or drive element of the rotary gear preferably comprises one free end and the drive-side or drive element of the stroke gear preferably comprises one free end, wherein the free end of the drive-side element of the stroke gear protrudes at least slightly beyond the free end of the drive-side element of the rotary gear.

The output-side or driven element of the rotary gear provided on the tool-holding device comprises a third element and the output-side element of the stroke gear provided on the tool-holding device comprises a fourth separate element and/or an element that is different from the third element. The third element or the output-side element of the rotary gear comprises a gearwheel, for example. The output-side or driven element of the rotary gear is preferably connected fixedly to the tool-holding device, so that the output-side element of the rotary gear is rotatably connected to the tool-holding device and is displaceable along the axis of rotation or the central axis of the tool-holding device.

The fourth element or the output-side element of the stroke gear comprises a setback, for example, or a groove, in particular an annular setback and/or a self-contained circular setback. The setback or groove is provided in particular in or on the tool-holding device, in particular in or on its outer surface or outer circumference or in or on a sleeve surrounding the tool-holding device, in particular in or on its outer surface or outer circumference.

The output-side or driven element of the rotary gear provided on the tool-holding device and the output-side element of the stroke gear provided on the tool-holding device are preferably disposed a distance apart from one another or are separated from one another, for example, by a shoulder or a step. The output-side element of the rotary gear and the output-side element of the stroke gear are preferably spaced a distance apart from one another such, that only the drive-side element of the rotary gear enters into a motion-generating and/or -transmitting connection with the output-side element of the rotary gear, and the drive-side element of the stroke gear enters into a motion-generating and/or -transmitting connection with the output-side element of the stroke gear.

The gearwheel, which is part of the first element or the drive-side element of the rotary gear, is disposed in particular concentrically around an axis of rotation of the single, joint driveshaft. The gearwheel can thus be induced only to a rotational movement by the single, joint driveshaft and is translationally stationary, in particular with respect to the central axis of the tool-holding device, i.e., a longitudinal movement or a stroke movement of the gearwheel with respect to the central axis of the tool-holding device cannot be induced by the single, joint driveshaft. If, as already described above, the output-side element of the rotary gear is displaceable with the tool-holding device along the axis of rotation or the central axis of the tool-holding device, but the drive-side element of the rotary gear is not thusly displaceable, then according to a particularly preferred embodiment, the output-side or driven element of the rotary gear is displaceable along the axis of rotation or the central axis of the tool-holding device relative to the drive-side element of the rotary gear.

The gearwheel, which is part of the first element or the drive-side element of the rotary gear, preferably comprises a sleeve, in which at least a section of the single, joint driveshaft is accommodated. The sleeve is preferably connected, in particular in one piece, to the gear rim of the gearwheel. The sleeve is preferably disposed adjacent a bearing sleeve for bearing support of the single, joint driveshaft.

Preferably at least a part of the drive-side element of the stroke gear, in particular the pin, is disposed inside the gearwheel, which is part of the first element or the drive-side element of the rotary gear. In particular at least a part of the drive-side element of the stroke gear extends through the gearwheel or into the interior of the gearwheel. Thus, the teeth of the gearwheel surround the drive-side element of the stroke gear, in particular the teeth surround the drive-side element in a circular shape. A particularly compact design of the hand element can thus be achieved in an advantageous manner. According to a preferred embodiment, which also constitutes an independent aspect of the invention, the drive-side or drive element, in particular the pin of the stroke gear, is provided concentrically around an axis of rotation of the driveshaft on which the drive-side element is provided and through which it can be induced to movement. The driveshaft is particularly preferably designed as a single, joint driveshaft, on which the drive-side or drive element of the rotary gear, in particular a gearwheel, is additionally disposed in agreement with the preceding. The driveshaft and the drive-side element of the stroke gear in particular have a common axis of rotation.

The drive-side or drive element of the stroke gear, which is disposed concentrically around an axis of rotation of the driveshaft, is preferably designed in one piece with the driveshaft or with the single, joint driveshaft. In particular the concentrically disposed element is designed as a protrusion or a stump, in particular as a pin-shaped protrusion or a stump on the (in particular single, joint) driveshaft. The element disposed concentrically is disposed in particular on one end or on one end face of the (in particular single, joint) driveshaft.

The drive-side or drive element of the stroke gear, which is disposed concentrically around an axis of rotation of the driveshaft is preferably designed such, that the tool-holding device passes through more than a double stroke, in particular at least two double strokes, in a complete rotation of the drive-side element of the stroke gear, i.e., in a 360° rotation. In other words, the tool-holding device in a complete revolution of the drive-side element of the stroke gear disposed concentrically can be moved from a starting position through an upward or forward stroke, a downward or reverse stroke, back into the starting position and beyond this starting position. Thus, an increase in the stroke frequency with respect to the rotational speed of the driveshaft or the tool-holding device can be achieved in an advantageous manner.

The drive-side element of the stroke gear disposed concentrically around an axis of rotation of the driveshaft preferably comprises a polygonal pin, in particular a pin having a polygonal cross section, which engages a setback in the output-side or driven element of the stroke gear on the tool-holding device in particular. The polygonal pin is preferably designed in one piece with the (in particular single, joint) driveshaft. The polygonal pin preferably comprises an odd number of corners or peaks, in particular three or five peaks. The polygonal pin preferably comprises outwardly bulging or convex exterior sides in particular. The polygonal pin is particularly preferably designed such, that (in cross section) the distance from a peak to the exterior side opposite said peak is constant along the entire exterior side. Particularly preferable the polygonal pin is designed as an orbiform element, for example, as a triangular or pentagonal orbiform element.

The output-side or driven element or the setback of the stroke gear on the tool-holding device, in which the concentrically disposed polygonal pin engages preferably comprises two opposing surfaces, in particular ring surfaces. Particularly preferable the polygonal pin or the orbiform element and the output-side element are dimensioned and/or designed and/or disposed such, that the polygonal pin or the orbiform element is in continuous contact with the two surfaces of the output-side element. This advantageously yields very smooth-running operation and generates little noise.

In the cross section the radius of the outwardly curved exterior sides of the concentrically disposed polygonal pin is preferably larger than the radius of the cylindrical outer cirumference of the single, joint driveshaft. Particularly preferably the distance from the axis of rotation to the outwardly curved exterior sides of the concentrically disposed polygonal pin in the cross section and relative to the axis of rotation of the single, joint driveshaft, is smaller than the radius of the cylindrical outer circumference of the single, joint driveshaft. Thus a particularly compact design of the driveshaft and the drive-side element of the stroke gear can be achieved in an advantageous manner.

According to an alternative embodiment, the drive-side or drive element of the stroke gear is disposed eccentrically to an axis of rotation of the single, joint driveshaft. The drive-side element of the stroke gear preferably comprises a cylindrical pin, which is preferably designed in one piece with the single, joint driveshaft and in particular engages the output-side or driven element of the stroke gear, for example, a setback on the tool-holding device. The cylindrical pin is preferably surrounded by a bushing, which is movable with the cylindrical pin.

As already explained above, the embodiment, according to which the drive-side element, in particular the pin of the stroke gear is disposed concentrically around an axis of rotation of the driveshaft, on which the drive-side element is provided and through which it can be set in movement, also constitutes an independent aspect of the invention. Such a stroke gear can thus also be implemented in any hand instrument, in particular in a medical or dental hand instrument, in which the tool-holding device can be set exclusively in a stroke or reciprocating movement (without any additional rotational movement of the tool-holding device, as described above). Accordingly, a medical or dental hand instrument according to a second embodiment comprises: a tool-holding device for fastening a treatment tool on the hand instrument, wherein the tool-holding device can be set in a stroke movement, a driveshaft for transmitting a drive movement to the tool-holding device and a stroke gear, which is designed to induce the tool-holding device to a stroke movement, wherein the stroke gear comprises a drive-side or drive element connected to the driveshaft, the drive-side element being disposed concentrically around an axis of rotation of the driveshaft.

The embodiment, according to which the stroke gear is designed so that the tool-holding device passes through more than a double stroke in a complete rotation of the drive-side or drive element of the stroke gear, also constitutes an independent aspect of the invention. Such a stroke gear can be implemented in any hand instrument, in particular in a medical or dental hand instrument, in which the tool-holding device can be set exclusively in a stroke movement (without additional rotational movement of the tool-holding device as described above). Accordingly a medical or dental hand instrument according to a third embodiment comprises: a tool-holding device for fastening a treatment tool on the hand instrument, wherein the tool-holding device can be set in a stroke movement, a driveshaft for transmitting a drive movement to the tool-holding device and a stroke gear, which is designed to induce the tool-holding device to a stroke movement, wherein the stroke gear comprises a drive-side or drive element connected to the driveshaft, said drive-side element being designed such, that in a complete revolution of the drive-side element, the tool-holding device passes through more than a double stroke.

The drive-side or drive element of the stroke gear of the second or third embodiment preferably comprises a polygonal pin, which engages in particular an output-side or driven element of the stroke gear, for example, a setback in or on the tool-holding device.

The preferred refinements and embodiments of the first embodiment of a medical or dental hand instrument described above can be used accordingly for the second or third embodiment of a medical or dental hand instrument or can be combined accordingly. Thus, the single joint driveshaft can also be referred to simply as the "driveshaft."

These and other embodiments will be described below with reference to the accompanying drawings.

DETAILED DESCRIPTION

Figure 1:
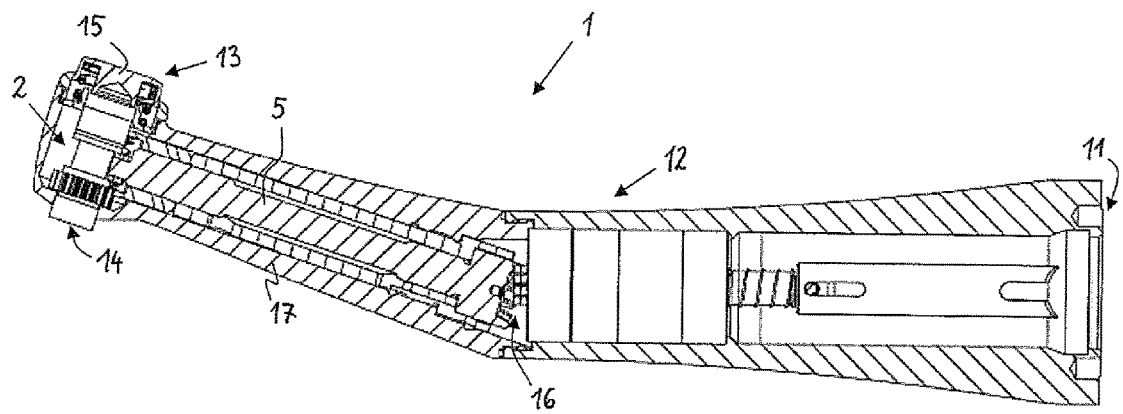
FIG. 1 shows a first embodiment of a medical or dental hand instrument comprising a tool-holding device, which can be induced to a simultaneous stroke and rotational movement through a rotary gear and a stroke gear, wherein the drive-side element of the rotary gear and the eccentrically disposed drive-side element of the stroke gear are provided on a single, joint driveshaft.
Figure 3:
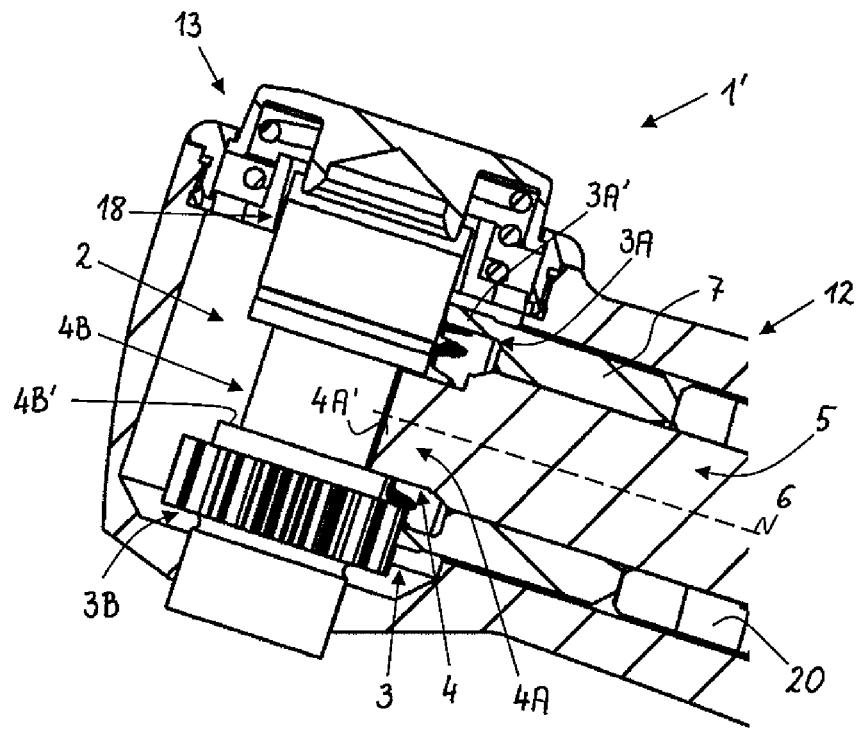
FIG. 3 shows a second embodiment of a medical or dental hand instrument having a tool-holding device, which can be induced to a simultaneous stroke and rotational movement by means of a rotary gear and a stroke gear, wherein the drive-side element of the rotary gear and the concentrically disposed drive-side element of the stroke gear are provided on a single joint driveshaft.

The medical, in particular dental, hand instrument 1, 1' shown in FIGS. 1 and 3 is designed as an elongated tubular instrument or handpiece that can be held in the hand. The hand instrument 1, 1' comprises an outer sleeve 17. A connecting device or coupling 11 for releasable connection to a control unit, for example, to a drive unit, to an energy source and/or to a fluid source, in particular a water and/or compressed air source, is provided on one end of the hand instrument 1, F. The hand instrument 1, 1' additionally comprises a curved handle part 12 or a handle part having two sections disposed at an angle to one another and a head section 13 connected thereto.

A tool opening 14, through which a tool for acting on a treatment site can be releasably introduced into the head section 13, is provided in the outer sleeve 17 of the head section 13. A releasable tool-holding device 2, comprising a chuck, for example, is disposed in the head section 13, securing the tool releasably on the head section 13. The tool opening 14 is disposed on the side of the head section 13, so that the tool protrudes out of the head section 13 at an angle to the handle part 12 or its longitudinal axis. A push button 15, which cooperates with a tool release device, which is disposed in the head section 13 to release the tool from the head section 13 or from the tool-holding device 2 is provided on the end of the head section 13 opposite the tool opening 14. The hand instrument 1, 1' may of course also have other known shapes, for example, may be designed to be straight or in the shape of gun, for example.

A device for transmitting driving energy to the tool-holding device 2 extends from the connecting device 11 through the handle part 12. The device for transmitting drive energy comprises, for example, at least one driveshaft 5 and/or at least one gear 16. The drive movement is then transferred from the driveshaft 5, which is disposed adjacent the head section 13, to the tool-holding device 2 through a gear unit having a rotary gear 3 and a stroke gear 4, as described in greater detail below.

Preferably also at least one fluid line or media line for water or compressed air, for example, and/or an optical waveguide and/or an electric power supply line or control lines extend(s) from the connecting device 11 through the handle part 12.

The design of the head sections 13 of the hand instrument 1 and of the hand instrument 1' are described below with reference to FIGS. 2 and 3:

The tool-holding device 2 for fastening a treatment tool to the hand instrument 1, 1' can be induced to a simultaneous stroke and rotational movement. The tool-holding device 2 comprises in particular an axis of rotation or a central axis 19, wherein it is designed to rotate about the central axis 19 and to be displaceable along the central axis 19, in particular to be displaceable alternately back and forth. Therefore, at least one bearing 18, in particular a friction bearing, which supports the tool-holding device 2 in such a way that the tool-holding device 2 can be induced to a simultaneous stroke and rotational movement, is provided in the head section 13.

To induce a rotational movement in the tool-holding device 2, a rotary gear 3 is provided. A stroke gear 4 is designed to induce the tool-holding device 2 to a stroke movement. The two gears 3, 4 are designed independently or separately from one another to transfer the rotary movement and to create the stroke movement.

The rotary gear 3 comprises at least one drive-side or drive element 3A, for example, a gearwheel 3A' and an output-side or driven element 3B, which is provided on the tool-holding device 2. The gearwheel 3A' is disposed concentrically around an axis of rotation 6 of the driveshaft 5. The output-side element 3B also comprises in particular a gearwheel. The output-side element 3B is disposed in particular between the tool opening 14 and a drive-side element 4A or an output-side element 4B of the stroke gear 4. The two elements 3A, 3B are designed and/or disposed in such a way that they are operatively connected to one another, in particular meshing with one another, so that a rotary movement can be transferred from the drive-side element 3A to the output-side element 3B.

The stroke gear 4 comprises at least one drive-side or drive element 4A and one output-side or driven element 4B provided on the tool-holding device 2. The drive-side element 4A comprises a pin 4A', 4A". The output-side element 4B of the stroke gear 4 is provided on the tool-holding device 2 or on a sleeve surrounding the tool-holding device 2 and comprises in particular a setback 4B' or an annular groove. The output-side element 4B of the stroke gear 4 is disposed in particular between the output-side element 3B of the rotary gear 3 and the push button 15.

The driveshaft 5 is designed for transmitting a rotary movement or it can be induced to a rotary movement about the axis of rotation 6. The driveshaft is designed as a single joint driveshaft 5 for the drive-side element 3A of the rotary gear 3 and for the drive-side element 4A of the stroke gear 4, so that the rotary gear 3 and the stroke gear 4 can be driven jointly and exclusively by this one joint driveshaft 5.

The drive-side or drive element 4A of the stroke gear 4, in particular the pins 4A', 4A" are preferably connected in one piece to the single, joint driveshaft 5. For connecting the single, joint driveshaft 5 to the drive-side element 3A of the rotary gear 3, in particular the gearwheel 3A', the drive-side element 3A comprises a sleeve 7, in which at least a section of the single, joint driveshaft 5 is accommodated, for example, by pressing. A bearing sleeve 20 for bearing of the single, joint driveshaft 5 and which is stationary with respect to the driveshaft 5, follows the sleeve 7.

At least a portion of the drive-side element 4A of the stroke gear 4, in particular at least a portion of the pin 4A', 4A" extends through the gearwheel 3A' or into the interior of the toothed row of the gearwheel 3A' disposed in the form of a ring, so that the teeth of the gearwheel 3A' surround the drive-side element 4A of the stroke gear 4.

As explained below, the hand instruments 1, 1' of FIGS. 2 and 3 differ in particular in the design and positioning of the drive-side elements 4A of the respective stroke gears 4.

Figure 2:
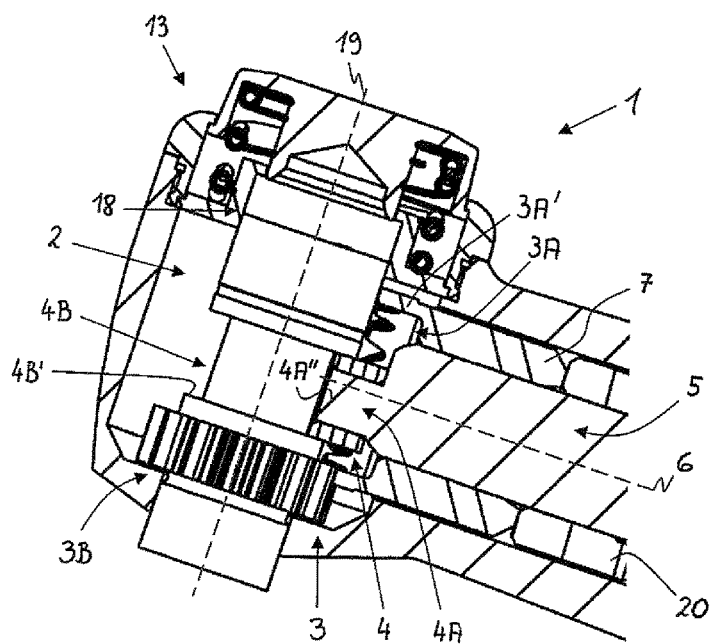
FIG. 2 shows an enlarged diagram of the head section of the hand instrument of FIG. 1.

The drive-side or drive element 4A of the stroke gear 4 of FIG. 2 is disposed eccentrically with the axis of rotation 6 of the single, joint driveshaft 5 and/or with the drive-side element 3A of the rotary gear 3, in particular to the toothed row of the gearwheel 3A' disposed in the form of a ring. The drive-side element 4A comprises a cylindrical pin 4A", which is preferably designed in one piece with the single, joint driveshaft 5. The cylindrical pin 4A" is of such dimensions and/or is disposed on a free end of the single, joint driveshaft 5 or on an end face of the driveshaft 5 such that it engages the output-side element 4B of the stroke gear 4 on the tool-holding device 2.

The drive-side or drive element 4A of the stroke gear 4 of FIG. 3 is disposed concentrically around the axis of rotation 6 of the single, joint driveshaft 5. The drive-side element 4A of the stroke gear 4 is additionally designed such, that with a complete revolution of the drive-side element 4A of the stroke gear 4 the tool-holding device 2 passes through more than a double stroke.

The drive-side element 4A of the stroke gear 4 of FIG. 3 comprises a polygonal pin 4A', which is preferably designed in one piece with the single, joint driveshaft 5 and engages the output-side or driven element 4B in the form of a ring-shaped setback 4W of the stroke gear 4 on the tool-holding device 2.

Figure 4A:
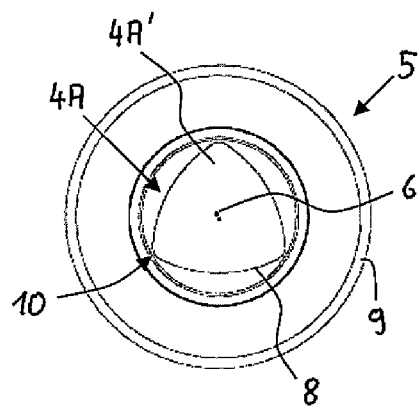
FIG. 4A shows a front view of a driveshaft and a drive-side element of the stroke gear disposed concentrically thereon and attached thereto.
Figure 4B:
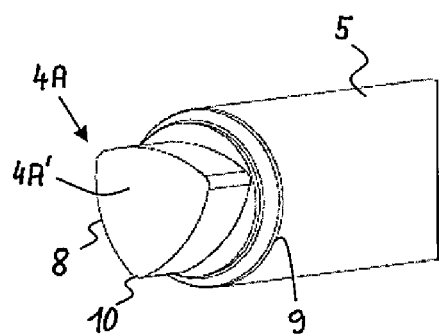
FIG. 4B shows a side view of the driveshaft and the drive-side element of the stroke gear of FIG. 4A disposed concentrically thereon and attached thereto.

The polygonal pin 4A' provided on the single, joint driveshaft 5 is shown in detail in FIGS. 4A, 4B. The polygonal pin 4A' has a triangular shape in cross section with three corners or peaks 10. The peaks 10 are joined together by outwardly bulging or convex exterior sides 8.

The outside dimension of the polygonal pin 4A' is smaller in cross section than the outside dimension of the single, joint driveshaft 5. In particular in the cross section, the radius of the outwardly bulging exterior sides 8 of the polygonal pin 4A' is larger than the radius of the cylindrical outer circumference 9 of the single, joint driveshaft 5.

The invention is not limited to the embodiments described here but instead includes all the embodiments that use or include the basic logical function principle of the invention. In addition all the features of all the embodiments described and presented here can be combined with one another.

What is claimed is:

1. A medical or dental hand instrument, comprising:
   a tool-holding device for fastening a treatment tool on the hand instrument, wherein the tool-holding device can be induced to a simultaneous stroke and rotational movement,
   a rotary gear set which is configured to induce the tool-holding device to the rotational movement and comprises at least one drive-side element and one output-side element which is coupled to the tool-holding device, a stroke gear set which is configured to induce the tool-holding device to the stroke movement and comprises at least one drive-side element and one output-side element which is coupled to the tool-holding device, a single drive shaft for transmitting a rotary movement on which the drive-side element of the rotary gear set and the drive-side element of the stroke gear set are disposed, the single drive shaft being driveable to drive the drive-side element of the rotary gear and the drive-side element of the stroke gear in rotation at the same rotational speed.

2. The medical or dental hand instrument according to claim 1, wherein the drive-side element of the rotary gear set comprises a gearwheel which is disposed concentrically around an axis of rotation of the single driveshaft.

3. The medical or dental hand instrument according to claim 2, wherein the gearwheel comprises a sleeve in which at least a section of the single driveshaft is accommodated.

4. The medical or dental hand instrument according to claim 2, wherein at least a portion of the drive-side element of the stroke gear set extends through the gearwheel, so that the teeth of the gearwheel surround the drive-side element of the stroke gear set.

5. The medical or dental hand instrument according to claim 2, wherein the gearwheel comprises a sleeve which is formed in one piece with the gearwheel and in which at least a section of the single driveshaft is accommodated.

6. The medical or dental hand instrument according to claim 1, wherein the drive-side element of the stroke gear set is disposed concentrically around an axis of rotation of the single driveshaft.

7. The medical or dental hand instrument according to claim 6, wherein the drive-side element of the stroke gear set is designed such that, with a complete revolution of the drive-side element of the stroke gear set, the tool-holding device passes through more than a double stroke.

8. The medical or dental hand instrument according to claim 6, wherein the drive-side element of the stroke gear set comprises a polygonal pin which engages the output-side element of the stroke gear set on the tool-holding device.

9. The medical or dental hand instrument according to claim 8, wherein the polygonal pin comprises outwardly bulging exterior sides.

10. The medical or dental hand instrument according to claim 9, wherein in cross section a radius of the outwardly bulging exterior sides of the polygonal pin is larger than a radius of the cylindrical outer circumference of the single driveshaft.

11. The medical or dental hand instrument according to claim 8, wherein the polygonal pin comprises three or five peaks.

12. The medical or dental hand instrument according to claim 1, wherein the drive-side element of the stroke gear set is disposed eccentrically to an axis of rotation of the single driveshaft.

13. The medical or dental hand instrument according to claim 12, wherein the drive-side element of the stroke gear set comprises a cylindrical pin which engages the output-side element of the stroke gear set on the tool-holding device.

14. The medical or dental hand instrument according to claim 1, wherein the output-side element of the rotary gear set comprises a gearwheel which is fixedly connected to the tool-holding device and rotates with the tool-holding device and is displaceable along an axis of rotation of the tool-holding device during the simultaneous stroke and rotational movement.

15. The medical or dental hand instrument according to claim 1, wherein the drive-side element of the stroke gear comprises an orbiform element.

16. A medical or dental hand instrument, comprising:
a tool-holding device for fastening a treatment tool on the hand instrument, wherein the tool-holding device can be induced to a stroke movement,
a driveshaft for transmitting a driving movement to the tool-holding device, and
a stroke gear set which couples the tool-holding device with the driveshaft and is configured to induce the tool-holding device to the stroke movement, wherein the stroke gear set comprises a drive-side element connected to the driveshaft, wherein
the drive-side element of the stroke gear set is disposed on the driveshaft and concentrically around an axis of rotation of the driveshaft,
a rotary gear set configured to induce the tool-holding device to a rotational movement and comprising a gearwheel which is disposed on the driveshaft concentrically around the axis of rotation of the driveshaft,
wherein the driveshaft transmits a rotary movement to the drive-side element of the stroke gear set and the gearwheel of the rotary gear set to drive the drive-side element of the stroke gear set and the gearwheel at the same rotational speed, and
wherein the drive-side element of the stroke gear set is configured such, that in a complete revolution of the drive-side element of the stroke gear set the tool-holding device runs through more than a double stroke.

17. The medical or dental hand instrument according to claim 16, wherein the drive-side element of the stroke gear set comprises a polygonal pin which engages an output-side element of the stroke gear set on the tool-holding device.

18. The medical or dental hand instrument according to claim 17, wherein the polygonal pin comprises outwardly bulging exterior sides.

19. The medical or dental hand instrument according to claim 16, wherein the stroke gear set further comprises an output-side element which is provided around the tool-holding device and comprises a self-contained, ring-shaped setback having two opposing surfaces, wherein
in an assembled state of the stroke gear set, the drive-side element of the stroke gear set is in continuous contact with the two surfaces of the output-side element.

20. A medical or dental hand instrument, comprising:
a tool-holding device for fastening a treatment tool on the hand instrument, wherein the tool-holding device can be induced to a simultaneous stroke and rotational movement,
a rotary gear set which is configured to induce the tool-holding device to the rotational movement and comprises at least one drive-side element and one output-side element which is coupled to the tool-holding device,
a stroke gear set which is configured to induce the tool-holding device to the stroke movement and comprises at least one drive-side element having an orbiform element and one output-side element which is coupled to the tool-holding device,
a single drive shaft for transmitting a rotary movement on which the drive-side element of the rotary gear set and the drive-side element of the stroke gear set are disposed, the single drive shaft being driveable to drive the drive-side element of the rotary gear and the drive-side element of the stroke gear in rotation at the same rotational speed.

* * * * *